United States Patent [19]

Vallet

[11] 4,151,291
[45] Apr. 24, 1979

[54] ETHERS OF 7-HYDROXY-COUMARIN USEFUL AS MEDICAMENTS

[75] Inventor: François M. J. Vallet, Paris, France

[73] Assignee: Unicler, Paris, France

[21] Appl. No.: 852,442

[22] Filed: Nov. 17, 1977

[30] Foreign Application Priority Data

Nov. 24, 1976 [FR] France .................. 76 35331

[51] Int. Cl.² .................... A61K 31/37; C07D 311/16
[52] U.S. Cl. .................... 424/281; 260/326; 260/8; 260/343; 260/44; 260/45; 544/151; 546/196
[58] Field of Search .................... 260/343.44; 424/281

[56] References Cited

U.S. PATENT DOCUMENTS 3,928,388  12/1975  Reichenbacher ............... 260/343.44

OTHER PUBLICATIONS

Murray et al., Tetrahedron letters, No. 3, pp. 243-244, 1970.
Theimer, Chem. Abstracts, vol. 79.
Matsubara, Chem. Abstracts, vol. 79.

Primary Examiner—Natalie Trousof
Assistant Examiner—Jane T. Fan
Attorney, Agent, or Firm—Stevens, Davis, Miller & Mosher

[57] ABSTRACT

The invention provides novel esters of 7-hydroxycoumarin of the formula

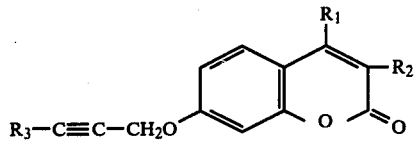

in which each of $R_1$ and $R_2$ represents a hydrogen atom, a $C_1$-$C_4$ alkyl, $C_2$-$C_4$ alkenyl, carboxy, carboxylate, $C_2$-$C_5$ alkoxycarbonyl or nitrophenyl group, and $R_3$ represents a hydrogen atom or a group of the formula —$CH_2$—Z in which Z represents a di($C_1$-$C_4$alkyl) amino group, or a saturated heterocyclic amino radical containing 5 to 7 ring members which may contain a further heteroatom, and their pharmaceutically acceptable acid addition salts. The compounds are useful as medicaments, in particular as analgesics.

13 Claims, No Drawings

ETHERS OF 7-HYDROXY-COUMARIN USEFUL AS MEDICAMENTS

The present invention relates to novel derivatives of coumarin useful as medicaments, notably as analgesics.

Coumarin derivatives useful as medicaments, in particular 4-methyl-7-hydroxy-coumarin, or hymecromone, sold as a choleretic, are already known.

According to the invention, there are provided novel ethers of 7-hydroxy-coumarin corresponding to the formula

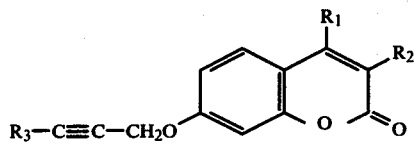

in which
each of $R_1$ and $R_2$, which may be the same or different, is selected from the group consisting of hydrogen atoms, alkyl and alkenyl groups containing up to 4 carbon atoms, carboxy groups, carboxylate groups, alkoxycarbonyl groups containing 2 to 5 carbon atoms, and nitrophenyl groups, and
$R_3$ is selected from the group consisting of hydrogen atoms and groups of the formula —$CH_2$—Z (in which Z is selected from the group consisting of dialkylamino groups in which each alkyl group contains 1 to 4 carbon atoms, and saturated heterocyclic amino radicals containing 5 to 7 ring members which may contain a further heteroatom).

The invention also provides pharmaceutically acceptable acid addition salts of the amines of the formula I (i.e. those compounds wherein $R_3$ represents a group of the formula —$CH_2$—Z).

Preferred compounds according to the invention are those in which $R_1$ represents a methyl group.

Particularly preferred compounds according to the invention are 3-allyl-4-methyl-coumarin and 4-methyl-7-(4-morpholino-but-2-ynyloxy)-coumarin, more particularly 4-methyl-7-propargyloxy-coumarin.

The compounds according to the invention may be prepared by reacting a 7-hydroxy-coumarin of the formula

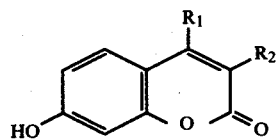

(wherein $R_1$ and $R_2$ are as defined above) with a propargyl halide, preferably propargyl bromide, to give a compound of the formula I in which $R_3$ represents a hydrogen atom and then, if necessary or desired, reacting the compound obtained with an appropriate amine of the formula

H—Z    (III)

(wherein Z is as defined above) and paraformaldehyde to give the corresponding compound of the formula I in which $R_3$ represents a group of the formula —$CH_2$—Z.

The reaction of the compound of the formula II with the propargyl halide may be effected, for example, by reacting the compound of the formula II with an approximately equal molar amount of the propargyl halide in a solvent such as acetone or dimethylformamide (DMF), in the presence of sodium or potassium carbonate.

The amine compounds of the formula I are preferably obtained by reacting the compound of the formula I wherein $R_3$ represents a hydrogen atom with approximately equimolar amounts of respectively the appropriate amine and paraformaldehyde, in the presence of cuprous iodide, in a solvent such as dioxane.

Amine compounds of the formula I may be reacted with pharmaceutically acceptable mineral or organic acids to form their pharmaceutically acceptable acid addition salts.

The compounds of the formula II, wherein $R_1$ is other than a hydrogen atom, may be prepared by reacting, in strongly acid medium, resorcinol with an acid of the formula

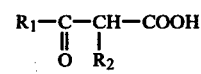

or a salt or ester of such an acid.

The compounds of the formula II in which $R_1$ represents a hydrogen atom may be prepared by for example reaction of 2,4-dihydroxybenzaldehyde with an acid of the formula $R_2CH_2COOH$    (V)

or a salt, anhydride or ester of such an acid.

To obtain the compounds of the invention, it is however also possible to prepare first the propargyloxy derivative of resorcinol or of 2,4-dihydroxybenzaldehyde, and then form the coumarin derivative by reaction of this propargyloxy derivative with the compound of the formula IV or V or derivative thereof.

The following Examples illustrate the invention without however placing any limitation thereon.

EXAMPLE 1

7-Propargyloxy-coumarin (JB 1)

In 100 ml DMF at 70° C. for 12 hours, 0.1 mole 7-hydroxy-coumarin is reacted with 0.1 mole propargyl bromide in the presence of 0.1 mole potassium carbonate. The compound of the title is obtained at a 60% yield. This compound melts at 118° C.

EXAMPLE 2

4-Methyl-7-propargyloxy-coumarin (JB 2)

0.1 mole resorcinol and 0.1 mole ethyl acetylacetate in solution in 100 ml concentrated sulphuric acid are maintained at 5° C. for 3 hours. After recyrstallisation of the solid formed from ethanol, there are obtained 12.5 grams 4-methyl-7-hydroxy-coumarin, melting at 185° C.

0.1 mole of this compound is dissolved in 100 ml acetone and reacted under reflux for 12 hours with 0.1 mole propargyl bromide in the presence of 0.1 mole potassium carbonate. The compound of the title is obtained at a 77% yield. After recrystallisation from ethanol, the compound melts at 138° C.

EXAMPLE 3

4-Carbethoxy-7-propargyloxy-coumarin (JB 3)

0.10 mole resorcinol and 0.12 mole sodium diethyl oxalacetate is heated to 80° C. for 1 hour in 60 ml concentrated phosphoric acid. 4-Carbethoxy-7-hydroxy-coumarin is thus obtained at an 80% yield in the form of a viscous oil.

0.1 mole of this compound is then reacted, in 100 ml acetone under reflux over 12 hours, with 0.1 mole propargyl bromide in the presence of 0.1 mole potassium carbonate. The ester of the title is obtained at a 60% yield. This ester melts at 110° C.

The corresponding acid is prepared by heating in 5% dilute alcoholic sodium hydroxide solution for one hour at 80° C. The 7-propargyloxy-coumarin-4-carboxylic acid obtained melts at 230° C.

EXAMPLE 4

3-Ethyl-4-methyl-7-propargyloxy-coumarin (JB 4)

0.1 mole resorcinol and 0.1 mole ethyl α-ethyl acetoacetate are heated at 80° C. for 20 minutes in 70 ml concentrated sulphuric acid. There are obtained 5.9 grams 3-ethyl-4-methyl-7-hydroxy-coumarin after recrystallisation from an ethanol-water (50/50) mixture. The compound melts at 200° C.

Then 0.1 mole of this compound is reacted, in 100 ml acetone under reflux for 12 hours, with 0.1 mole propargyl bromide in the presence of 0.1 mole potassium carbonate. The compound of the title is obtained at a 76% yield. This compound melts at 82° C.

EXAMPLE 5

3-Allyl-4-methyl-7-propargyloxy-coumarin (JB 19)

0.1 mole resorcinol and 0.1 mole ethyl α-allyl acetoacetate are heated at 80° C. for 20 minutes in 70 ml concentrated sulphuric acid. After recrystallisation from an ethanol-water (50/50) mixture, there are obtained 6.25 grams 3-allyl-4-methyl-7-hydroxy-coumarin. This compound melts at 198° C.

Then, in 100 ml acetone under reflux for 12 hours, 0.1 mole of this compound is reacted with 0.1 mole propargyl bromide in the presence of 0.1 mole potassium carbonate. The compound of the title is obtained at a yield of 66%. This compound melts at 120° C.

EXAMPLE 6

4-o-nitrophenyl-7-propargyloxy-coumarin (JB 5)

0.1 mole resorcinol is reacted with 0.1 mole ethyl o-nitrobenzoylacetate in methanol at 0° C. while passing through for one hour gaseous hydrochloric acid, and then maintaining at ambient temperature for 24 hours. After recrystallisation from an acetone-water mixture, there are obtained 18 grams 4-o-nitrophenyl-7-hydroxy-coumarin. This compound melts at 230° C.

Then 0.1 mole of this compound is reacted, in 100 ml acetone under reflux for 12 hours, with 0.1 mole propargyl bromide in the presence of 0.1 mole potassium carbonate. The compound of the title is obtained at a 67% yield. This compound melts at 156° C.

EXAMPLE 7

4-Methyl-3-carbethoxy-7-propargyloxy coumarin (JB 6)

0.1 mole resorcinol is reacted with 0.1 mole diethyl acetylmalonate for 20 minutes at 70° C. in 70 ml concentrated sulphuric acid. After recrystallisation from an ethanol-water mixture, 3 grams 4-methyl-3-carbethoxy-7-hydroxy-coumarin are obtained. This compound melts at 132° C.

Then 0.1 mole of this compound is reacted, in 100 ml acetone under reflux for 27 hours, with 0.1 mole propargyl bromide in the presence of 0.1 mole potassium carbonate. The ester of the title is obtained at a 60% yield. This compound melts at 78° C.

The corresponding acid (JB 7) is prepared by heating in 5% dilute alcoholic sodium hydroxide solution for 1 hour at 80° C. The 4-methyl-7-propargyl-coumarin-3-carboxylic acid obtained melts at 172° C.

EXAMPLE 8

3-Carbethoxy-7-propargyloxy-coumarin (JB 8)

0.1 mole 2,4-dihydroxybenzaldehyde is reacted with 0.15 mole diethyl malonate at 80° C. for 24 hours in ethanol in the presence of a few ml piperidine. After recrystallisation from ethanol, 12 grams 3-carbethoxy-7-hydroxy-coumarin are obtained. This compound melts at 172° C.

Then, in 100 ml acetone under reflux for 36 hours, 0.1 mole of this compound is reacted with 0.1 mole propargyl bromide in the presence of 0.1 mole potassium carbonate. The compound of the title is obtained at a yield of 65%. This compound melts at 154° C.

The corresponding acid (JB 9) is prepared by heating in 5% dilute alcoholic sodium hydroxide solution for 1 hours at 80° C. The 7-propargyloxy-coumarin-3-carboxylic acid obtained melts at 252° C.

EXAMPLE 9

3-Methyl-7-propargyloxy-coumarin (JB 10)

In 100 ml acetone at 58° C. for 3 hours, 0.1 mole 2,4-dihydroxybenzaldehyde is reacted with 0.1 mole propargyl bromide, in the presence of potassium carbonate. After recrystallisation from an ethanol-water mixture, 10 grams 4-propargyloxy-2-hydroxybenzaldehyde are obtained. This compound melts at 78° C.

0.08 mole of this compound is reacted with 0.16 mole sodium propionate and 0.16 mole propionic acid anhydride at 180° C. for 9 hours. After recrystallisation from benzene, 8 grams of the compound of the title are obtained. This compound melts at 154° C.

EXAMPLE 10

4-Methyl-7-(4-morpholino-but-2-ynyloxy)-coumarin (JB 11) and its hydrochloride (JB 12)

21.5 grams 4-methyl-7-propargyloxy-coumarin, 8.5 grams morpholine, 3.3 grams paraformaldehyde and 2 grams $Cu_2I_2$ are maintained in 100 ml dioxane at 60° to 70° C. for 5 to 6 hours. The reaction mixture is poured into water, filtered and recyrstallised from cyclohexane. 18 grams of the base of the title are obtained. This compound melts at 126° C.

The corresponding hydrochloride is prepared by subjecting the base to a stream of hydrogen chloride gas in acetone. After recrystallisation from absolute alcohol, the hydrochloride obtained (JB 12) melts at 225° C. (instantaneously).

EXAMPLE 11

4-Methyl-7-(4-piperidino-but-2-ynyloxy)-coumarin (JB 13) and its hydrochloride (JB 14)

This Example is carried out using the method of Example 10 but replacing the morpholine by piperidine.

The base is obtained at a yield of 48%. This compound melts at 120° C.

After recrystallisation from absolute alcohol, the corresponding hydrochloride (JB 14) melts at 228° C. (instantaneously).

EXAMPLE 12

4-Methyl-7-(4-dimethylamino-but-2-ynyloxy)-coumarin (JB 15) and its hydrochloride (JB 16)

This Example is carried out using the method of Example 10 but replacing the morpholine by dimethylamine.

The base of the title is obtained at a yield of 52%. This compound melts at 102° C.

After recyrstallisation from absolute alcohol, the corresponding hydrochloride (JB 16) melts at 210° C. (instantaneously).

EXAMPLE 13

4-Methyl-7-(4-pyrrolidino-but-2-ynyloxy)-coumarin (JB 17) and its hydrochloride (JB 18)

This Example is carried out using the method of Example 10 but replacing the morpholine by pyrrolidine.

The base of the title is obtained at a yield of 54%. This compound melts at 110° C.

After recrystallisation from absolute alcohol, the corresponding hydrochloride (JB 18) melts at about 220° C. (instantaneously).

The compounds according to the invention have been subjected to pharmacological tests in order to show their therapeutic activity.

They have in particular been submitted to the test of analgesia of Siegmund, Cadmus and Lu (Proc. Soc. Exp. Biol. Med. 95, 729, 1957) according to which a characteristic pain syndrome is provoked in mice by injection of phenylbenzoquinone.

The animals used are mice of Swiss strain weighing 20±2 grams.

The animals are separated into groups of 10, randomly but are individually submitted to experiments. Each experiment is carried out on at least two groups:
- a control group receiving solvent and phenylbenzoquinone
- a group treated with test compound.

The test compounds are administered orally, 30 minutes before the injection of the irritant. Each mouse then receives intraperitoneally 0.25 ml of a 0.02% phenylbenzoquinone solution.

The pain syndrome generated by the injection of phenylbenzoquinone consists of extension of the abdomen and the back legs; at the height of the reaction, the flanks of the animal are very contracted. 5 Minutes after the injection of the irritant, the extensions are counted over a period of 10 minutes.

For each group, the mean number of extensions is calculated. The activity (A) of the test compound is determined by comparison between the mean number of extensions in the treated animals (N) and the mean number of extensions in the control animals (N') according to the equation $$A = \frac{N' - N}{N'} \times 100$$

The statistical significance of the result thus obtained is evaluated by the non-parametric test of Fisher.

In addition the oral $LD_{50}$ was determined for the compounds of the invention.

The results obtained are shown in the following Table

| Compound | $LD_{50}$ mg/kg | Analgesic Activity dose in mg/kg → A |
|---|---|---|
| JB 1 | 1500 | 150 → 55% |
| JB 2 | 1500 | 150 → 98% |
| JB 4 | 1000 | 100 → 65% |
| JB 19 | 1500 | 150 → 81% |
| JB 5 | >>2000 | 200 → 40% |
| JB 12 | 1500 | 150 → 88% |
| JB 16 | 500 | 50 → 30% |

The compounds of the invention show valuable analgesic activity making them utilisable for example in the treatment of chronic and acute pain, traumatic algias, rheumatic, visceral and neurologic, dental pains and diverse algias such as headaches, cancerous pain, etc.

Accordingly the invention also provides a method of treating a human patient which method comprises administering to the patient an analgesically effective amount of a compound according to the invention.

The compounds of the invention may be presented in conventional pharmaceutical administration forms such as tablets, capsules, suppositories and injectable forms, in association with pharmaceutically acceptable excipients and optionally other active ingredients.

The daily administration doses for an adult may vary between 50 and 1000 mg and preferably between 75 and 300 mg, orally.

The following are examples of administration forms:

| TABLET | |
|---|---|
| JB 2 | 75 mg |
| lactose | 25 mg |
| icing sugar | 10 mg |
| corn starch | 25 mg |
| alginic acid | 15 mg |
| other excipients qsp | 1 tablet at 200 mg |

The posology may be 1 to 4 tablets per day.

| CAPSULE | |
|---|---|
| JB 2 | 75 mg |
| corn starch | 105 mg |
| mannitol | 11 mg |
| alginic acid | 1 mg |
| sodium alginate | 0.1 mg |
| talc | 6 mg |
| palmitostearic ester of glycerol | 3 mg |
| For a capsule of about 200 mg. | |

I claim:
1. A compound of the formula

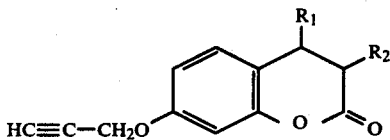

wherein each of $R_1$ and $R_2$ is independently hydrogen, $C_{1-4}$ alkyl, $C_{1-4}$ alkenyl, carboxy, $C_{2-5}$ alkoxycarbonyl or nitrophenyl, or a pharmaceutically acceptable salt thereof.

2. A compound of claim 1 of the formula:

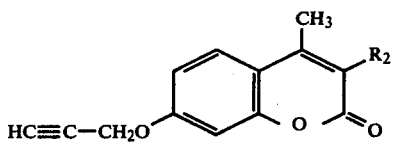

wherein $R_2$ is hydrogen, $C_{1-4}$ alkyl, $C_{1-4}$ alkenyl, carboxy, $C_{2-5}$ alkoxycarbonyl or nitrophenyl, or a pharmaceutically acceptable acid addition salt thereof.

3. A compound according to claim 2 which is 4-methyl-7-propargyloxy-coumarin.

4. A compound according to claim 2 which is 3-allyl-4-methyl-7-propargyloxy-coumarin.

5. An analgesic composition in dosage unit form comprising as active ingredient an analgesically effective amount of a compound of the formula:

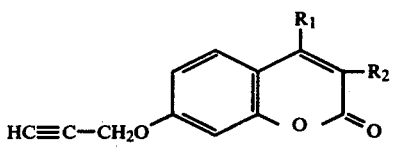

wherein each of $R_1$ and $R_2$ is independently hydrogen, $C_{1-4}$ alkyl, $C_{1-4}$ alkenyl, carboxy, $C_{2-5}$ alkoxycarbonyl or nitrophenyl; or a pharmaceutically acceptable salt thereof.

6. An analgesic composition according to claim 5 wherein $R_1$ is methyl.

7. An analgesic composition according to claim 5 wherein said compound is 4-methyl-7-propargyloxy-coumarin.

8. An analgesic composition according to claim 5 wherein said compound is 3-allyl-4-methyl-7-propargyloxy-coumarin.

9. A composition of claim 5 in the form of a tablet.

10. A composition of claim 5 in the form of a capsule.

11. A method of providing an analgesic effect to a patient which comprises administering to said patient an analgesically-effective amount of a compound of the formula:

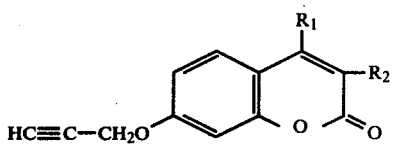

wherein each of $R_1$ and $R_2$ is independently hydrogen, $C_{1-4}$ alkyl, $C_{1-4}$ alkenyl, carboxy, $C_{2-5}$ alkoxycarbonyl or nitrophenyl; or a pharmaceutically acceptable salt thereof.

12. A method of claim 11, wherein $R_1$ is methyl.

13. A method of claim 12 wherein said compound is of the formula:

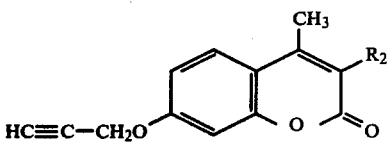

wherein $R_2$ is $C_{1-4}$ alkyl, $C_{1-4}$ alkenyl, carboxy, $C_{2-5}$ alkoxycarbonyl or nitrophenyl, or a pharmaceutically acceptable acid addition salt thereof.

* * * * *